United States Patent
Uenishi et al.

(10) Patent No.: US 7,248,996 B2
(45) Date of Patent: Jul. 24, 2007

(54) VEHICLE-OCCUPANT FATIGUE-LEVEL ASSESSMENT METHOD, VEHICLE SEAT ASSESSMENT METHOD, AND VEHICLE SEAT ASSESSMENT DEVICE

(75) Inventors: Koro Uenishi, Moriyama (JP); Masatoshi Tanaka, Omihachiman (JP); Naoki Miyamoto, Yasu (JP); Sadami Tsutsumi, Kyoto (JP)

(73) Assignee: Daihatsu Motor Co., Ltd., Osaka (JP)

( * ) Notice: Subject to any disclaimer, the term of this patent is extended or adjusted under 35 U.S.C. 154(b) by 115 days.

(21) Appl. No.: 10/525,931

(22) PCT Filed: Jun. 23, 2003

(86) PCT No.: PCT/JP03/07967

§ 371 (c)(1),
(2), (4) Date: Feb. 25, 2005

(87) PCT Pub. No.: WO2004/020963

PCT Pub. Date: Mar. 11, 2004

(65) Prior Publication Data

US 2006/0106562 A1    May 18, 2006

(30) Foreign Application Priority Data

Aug. 28, 2002 (JP) ............................. 2002-249020

(51) Int. Cl.
*G01L 5/00* (2006.01)

(52) U.S. Cl. ..................................................... 702/173

(58) Field of Classification Search ................ 702/173, 702/101, 113; 177/25.11; 700/305
See application file for complete search history.

(56) References Cited

U.S. PATENT DOCUMENTS 6,927,694 B1 *   8/2005   Smith et al. ................ 340/576
2004/0044293 A1 *   3/2004   Burton ........................ 600/544

FOREIGN PATENT DOCUMENTS

| JP | 1164131    | 6/1989  |
|----|------------|---------|
| JP | 6144071    | 5/1994  |
| JP | 9098851    | 4/1997  |
| JP | 10274577   | 10/1998 |
| JP | 11248409   | 9/1999  |
| JP | 11326084   | 11/1999 |
| JP | 2003118458 | 4/2003  |
| JP | 2004288990 | 10/2004 |

* cited by examiner

*Primary Examiner*—John Barlow
*Assistant Examiner*—Tung S. Lau
(74) *Attorney, Agent, or Firm*—The Webb Law Firm

(57) ABSTRACT

A highly reliable vehicle driver's fatigue evaluating method is provided, which is capable of quantitatively calculating a degree of fatigue of a driver seated on a seat. The degree of fatigue of the driver seated on a seat is quantitatively calculated based on an amount of rearward deflection of a lower part of a backrest portion of the seat, a load applied downward to a front part of a seating portion of the seat, and a load applied rearward to an upper part of the backrest portion, in a state of the driver being seated on the seat.

5 Claims, 7 Drawing Sheets

FIG.4
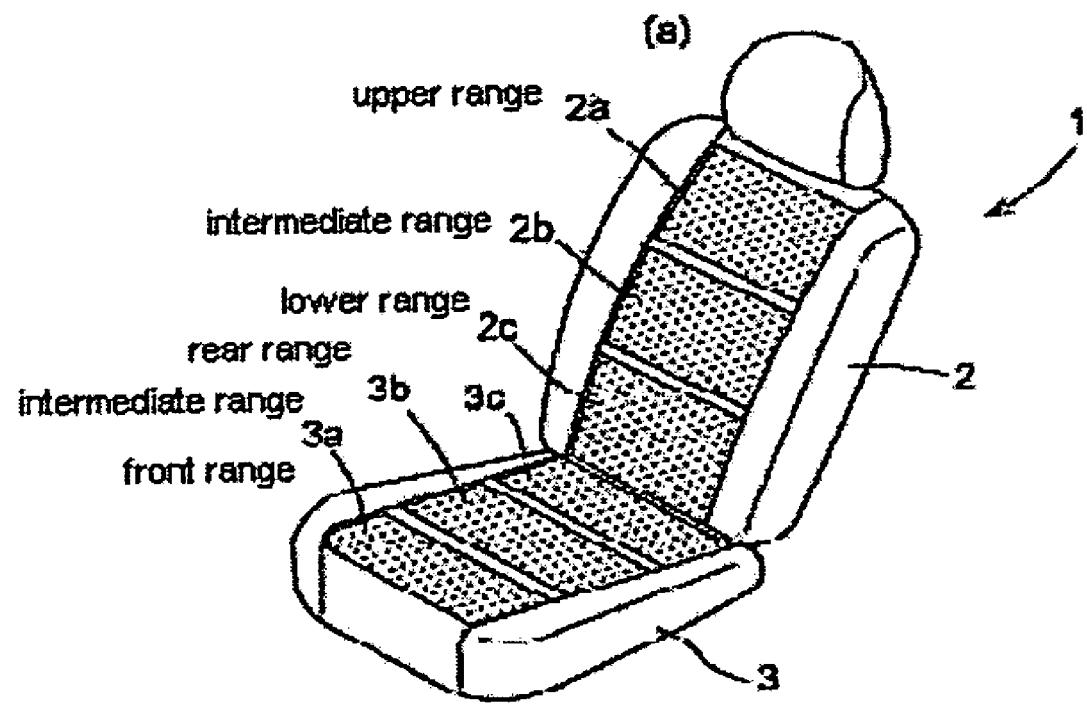
(a)
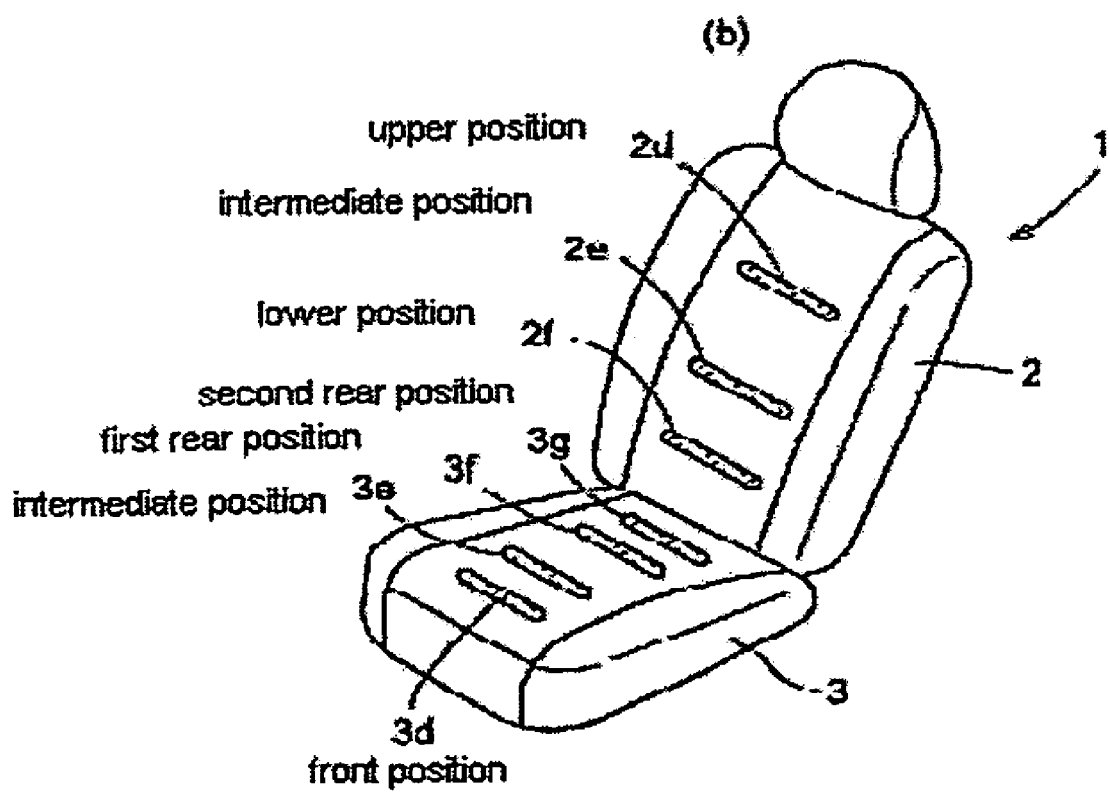
(b)

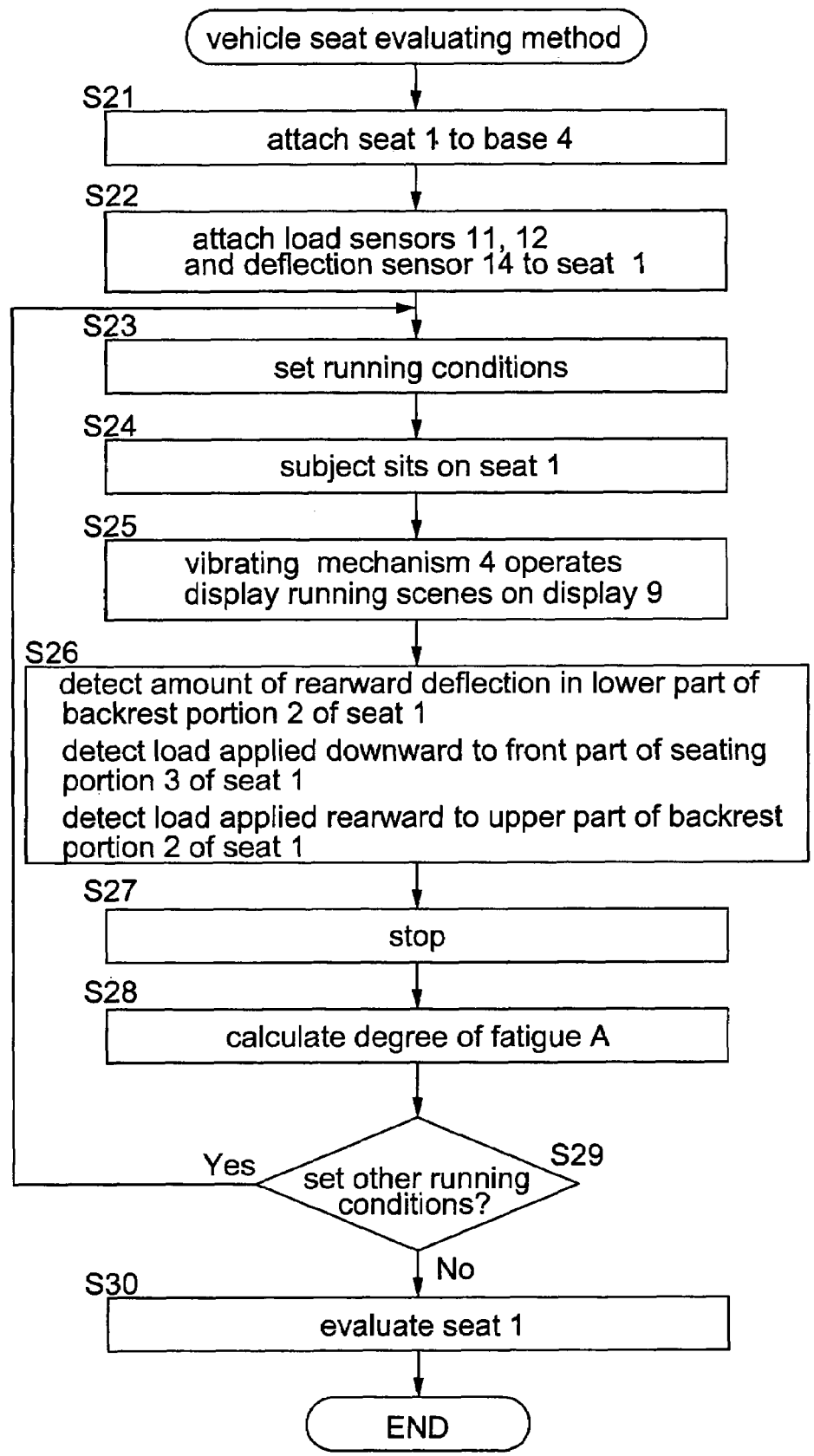

VEHICLE-OCCUPANT FATIGUE-LEVEL ASSESSMENT METHOD, VEHICLE SEAT ASSESSMENT METHOD, AND VEHICLE SEAT ASSESSMENT DEVICE

BACKGROUND OF THE INVENTION

1. Field of the Invention

The present invention relates to a vehicle driver's fatigue evaluating method for evaluating a degree of fatigue of a driver sitting on a seat of a vehicle such as a passenger vehicle, commercial vehicle or a bus, and to a vehicle seat evaluating method and vehicle seat evaluating apparatus using this vehicle driver's fatigue evaluating method.

2. Description of Related Art

In order to improve comfort in vehicles, development is desired of seats that cause little fatigue after a long sitting. To reduce the fatigue of the waist in particular is effective for relieving the fatigue of the whole body for the driver sitting on the seat.

The vehicle driver's fatigue evaluating method includes a method in which a subject is asked to enter a feeling of seating and a feeling of fatigue (especially a feeling of fatigue of the waist) on an evaluation sheet, and a method in which the fatigue of the waist of a subject is evaluated by detecting the myoelectric potential of the waist, both after the subject is actually seated on a seat for a long time.

As described in the prior art, a problem of low reliability occurs with the method in which the subject is asked to enter a feeling of seating and a feeling of fatigue on an evaluation sheet. This is because the subject's subjectivity tends to influence the evaluation of the feeling of seating and the feeling of fatigue (especially a feeling of fatigue of the waist), and an objective and quantitative evaluation of the fatigue of the driver sitting on a seat is impossible.

In the method in which the fatigue of the waist of a subject is evaluated by detecting the myoelectric potential of the waist, the myoelectric potential detected is prone to noise (spike noise, i.e. noise of very small pulse width resulting from switching operations). The fatigue of the driver sitting on a seat cannot be evaluated properly only by detecting the myoelectric potential of the subject's waist. Further, its validity is not positive with respect to the existence of correlation between the fatigue of the driver sitting on the seat and the myoelectric potential of the subject's waist.

The object of the present invention is to provide a highly reliable vehicle driver's fatigue evaluating method capable of quantitatively calculating a degree of fatigue of a driver seated on a seat, and to provide a highly reliable vehicle seat evaluating method and vehicle seat evaluating apparatus using this vehicle driver's fatigue evaluating method.

SUMMARY OF THE INVENTION

[I]

According to a first characteristic feature of the present invention, a vehicle driver's fatigue evaluating method is provided for quantitatively calculating a degree of fatigue of a driver seated on a seat based on an amount of rearward deflection of a lower part of a backrest portion of the seat, a load applied downward to a front part of a seating portion of the seat, and a load applied rearward to an upper part of the backrest portion, in a state of the driver being seated on the seat.

In quantitatively calculating a degree of fatigue of the driver seated on the seat, detection values other than a subjective evaluation by a subject and a myoelectric potential of the waist of the subject include a load applied rearward to an upper part of the backrest portion, a load applied rearward to an intermediate part of the backrest portion, a load applied rearward to a lower part of the backrest portion, an amount of rearward deflection of the upper part of the backrest portion, an amount of rearward deflection of the intermediate part of the backrest portion, an amount of rearward deflection of the lower part of the backrest portion, a load applied downward to a front part of the seating portion, a load applied downward to an intermediate part of the seating portion, a load applied downward to a rear part of the seating portion, an amount of downward deflection of the front part of the seating portion, an amount of downward deflection of the intermediate part of the seating portion, and an amount of downward deflection of the rear part of the seating portion.

Experiments carried out by Applicant herein have shown that, among the above detection values, the three detection values, i.e. the amount of rearward deflection of the lower part of the backrest portion, the load applied downward to the front part of the seating portion and the load applied backward to the upper part of the backrest portion, greatly influence the degree of fatigue of the driver seated on the seat.

These amounts of deflection and loads are free from the subject's subjectivity. Since the amounts of deflection of the seat and the loads applied to the seat, which are not a subject, are detected, noise (spike noise) will not occur. Thus, a highly reliable vehicle driver's fatigue evaluating method is provided according to this characteristic feature.

[II]

According to a second characteristic feature of the present invention, the degree of fatigue of the driver seated on the seat is calculated quantitatively by using an operational expression determined by a statistical technique.

According to this characteristic feature, the degree of fatigue of the driver seated on the seat may be obtained properly by adopting a multivariable function of the degree of fatigue of the driver seated on the seat, using the amount of rearward deflection of the lower part of the backrest portion, the load applied downward to the front part of the seating portion and the load applied backward to the upper part of the backrest portion as variables.

[III]

According to a third characteristic feature of the present invention, the operational expression noted in section [II] above is obtained by a multiple regression analysis with the amount of rearward deflection of the lower part of the backrest portion, the load applied downward to the front part of the seating portion and the load applied rearward to the upper part of the backrest portion regarded as explanatory variables, and an actual degree of fatigue measured of the driver seated on the seat as a response variable.

Multiple regression analysis is a typical example of the operational expression determined by statistical technique. A highly reliable operational expression is obtained by selecting detection values giving a high contribution, i.e. the amount of rearward deflection of the lower part of the backrest portion, the load applied downward to the front part of the seating portion and the load applied rearward to the upper part of the backrest portion, as explanatory variables, as in third characteristic feature of the invention.

[IV]

In order to obtain a seat that causes little fatigue even after a long sitting, it is effective to lessen especially fatigue of the waist in lightening fatigue of the whole body for the driver seated on the seat.

According to a fourth characteristic feature of the present invention, fatigue of the waist of the driver seated on the seat is made an actual degree of fatigue measured to the driver seated on the seat. Based on a viscoelastic property of muscles of the waist of the driver seated on the seat, fatigue of the waist of the driver seated on the seat (an actual degree of fatigue measured of the driver seated on the seat) is determined.

In this case, the viscoelastic property of the muscles of the waist of the driver seated on the seat can be measured by using a vibrator such as a piezoelectric element. Fatigue of the waist of the driver seated on the seat may be determined with high accuracy while suppressing a generation of noise (spike noise). This promotes the reliability of the vehicle driver's fatigue evaluating method.

[V]

According to a fifth characteristic feature of the present invention, a vehicle seat evaluating method is provided for evaluating the seat with the degree of fatigue of the driver seated on the seat calculated by the vehicle driver's fatigue evaluating method described in the foregoing sections [I] to [IV].

According to this, the seat may be evaluated reliably in connection with the degree of fatigue of the driver seated on the seat. Based on the vehicle seat evaluating method of the fifth characteristic feature of the invention, the shape and material of the seat may be changed, thereby to obtain a seat causing a reduced degree of fatigue of the driver seated on the seat.

[VI]

According to a sixth characteristic feature of the present invention, a vehicle seat evaluating apparatus is provided which comprises a first detecting device for detecting an amount of rearward deflection of a lower part of a backrest portion of a seat, a second detecting device for detecting a load applied downward to a front part of a seating portion of the seat, and a third detecting device for detecting a load applied rearward to an upper part of the backrest portion, in a state of the driver being seated on the seat; a calculating device for quantitatively calculating a degree of fatigue of the driver seated on the seat based on detection values of said first, second and third detecting devices; and an evaluating device for evaluating the seat by the degree of fatigue calculated by said calculating device.

According to this, the first, second and third detecting devices and the calculating device realizes a calculation of the degree of fatigue of the driver seated on the seat, free from the subject's subjectivity and without noise (spike noise) as described in the foregoing section [I]. The seat may be evaluated reliably in connection with the degree of fatigue of the driver seated on the seat.

BRIEF DESCRIPTION OF THE DRAWINGS

FIG. 4 is perspective views showing states of the vehicle seat evaluating apparatus detecting loads applied rearward to an upper range, an intermediate range and a lower range of a backrest of the seat, loads applied downward to a front range, an intermediate range and a rear range of a seating portion, amounts of rearward deflection in an upper position, an intermediate position and a lower position of the backrest, and amounts of downward deflection in a front position, an intermediate position, and a first and a second rear positions of the seating portion;

FIG. 8 is a view showing a flow of a vehicle seat evaluating method.

DETAILED DESCRIPTION OF THE INVENTION

[1]

Figure 6:
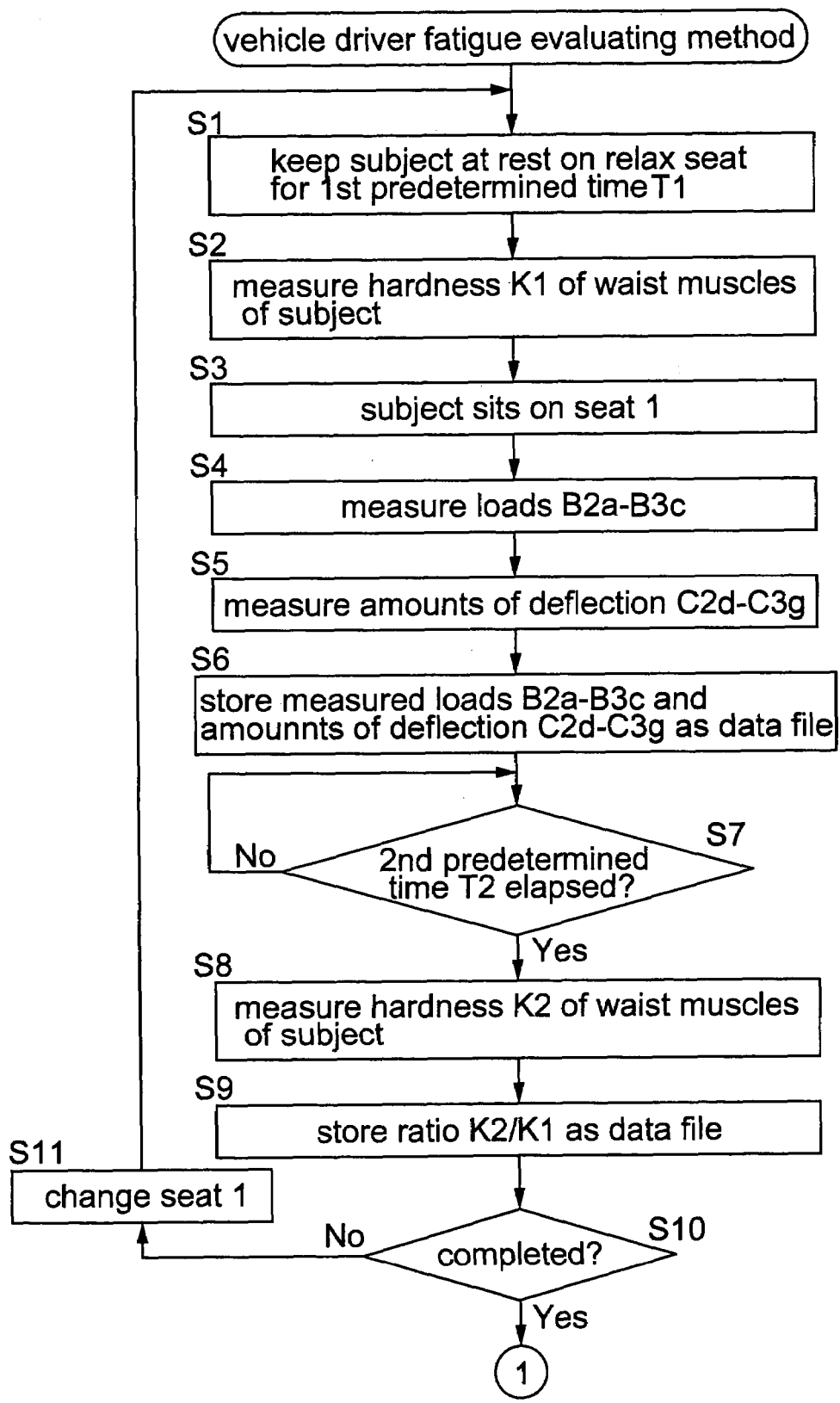
FIG. 6 is a view showing a flow of the first half of the vehicle driver's fatigue evaluating method.

The first half of a vehicle driver's fatigue evaluating method for quantitatively calculating a degree of fatigue A of a driver sitting on a seat 1 will be described with reference to FIGS. 4 and 6.

As shown in FIG. 4(a), the seat 1 constructed of pads of predetermined shape and predetermined material has a plurality of pressure sensors (not shown) arranged in each of an upper range 2a, an intermediate range 2b and a lower range 2c of a backrest portion 2 of the seat 1, and a front range 3a, an intermediate range 3b and a rear range 3c of a seating portion 3 of the seat 1. As shown in FIG. 4(b), the same seat 1 has a deflection sensor (not shown) arranged in each of an upper position 2d, an intermediate position 2e and a lower position of 2f of the backrest portion 2 and a front position 3d, an intermediate position 3e and a first and a second rear positions 3f and 3g of the seating portion 3.

First, a subject is kept at rest on a relax seat (not shown) different from the above seat 1 for a first predetermined time T1 (e.g. for 15 minutes) (step S1). Then, as described in [3] hereinafter, a viscoelastic property K1 (details will be described hereinafter) of the muscles the subject's waist is measured (step S2).

Next, the subject is asked to sit on the above seat 1 (step S3). Immediately after the subject sits down on the seat 1, measurements are taken through the pressure sensors of a load B2a applied rearward to the upper range 2a of the backrest portion 2, a load B2b applied rearward to the intermediate range 2b of the backrest portion 2, a load B2c applied rearward to the lower range 2c of the backrest portion 2, a load B3a applied downward to the front range 3a of the seating portion 3, a load B3b applied downward to the intermediate range 3b of the seating portion 3, and a load B3c applied downward to the rear range 3c of the seating portion 3.

In this case, regarding the detection values of the plurality of pressure sensors arranged in the upper range 2a of the backrest portion 2, for example, an average of the plurality of detection values is regarded as the load B2a applied rearward to the upper range 2a (upper part) of the backrest portion 2. Similarly, the load B2b applied rearward to the intermediate range 2b (intermediate part) of the backrest portion 2, the load B2c applied rearward to the lower range 2c (lower part) of the backrest portion 2, the load B3a applied downward to the front range 3a (front part) of the seating portion 3, the load B3b applied downward to the intermediate range 3b (intermediate part) of the seating portion 3 and the load B3c applied downward to the rear range 3c (rear part) of the seating portion 3 are determined (step S4).

Immediately after the subject sits down on the seat 1, measurements are taken through the deflection sensors of an amount of rearward deflection C2d in the upper position 2d (upper part) of the backrest portion 2, an amount of rearward deflection C2e in the intermediate position 2e (intermediate part) of the backrest portion 2, an amount of rearward deflection C2f in the lower position 2f (lower part) of the backrest portion 2, an amount of downward deflection C3d in the front position 3d (front part) of the seating portion 3, an amount of downward deflection C3e in the intermediate position 3e (intermediate part) of the seating portion 3, an amount of downward deflection C3f in the first rear position 3f (first rear part) of the seating portion 3, and an amount of downward deflection C3g in the second rear position 3g (second rear part) of the seating portion 3 (step S5). The loads B2a–B3c and amounts of deflection C2d–C3g measured are stored as a data file (step S6).

The subject remains seated on the seat 1 after the subject sits down on the seat 1 until elapse of a second predetermined time T2 (e.g. for three hours). When the second predetermined time elapses after the subject sits on the seat 1 (step S7), as described in [3] hereinafter, a viscoelastic property K2 of the muscles of the subject's waist is measured (step S8). Then, a ratio (K2/K1) between the viscoelastic property K1 of the muscles of the subject's waist measured in the above step S2 and the viscoelastic property K2 of the muscles of the subject's waist measured in step S8 is determined. The ratio (K2/K1) is regarded as an actual degree of fatigue measured of the driver seated on the seat 1, and the ratio (K2/K1) is stored as a data file (step S9). The measurement concerning the one seat 1 is completed as described above.

Next, the seat 1 is replaced with a seat 1 constructed of pads of different shape and different material (steps S10 and S11), and the same operation as in above steps S1–S9 is carried out. The same operation as in above steps S1–S9 is carried out for plural types of seat 1.

[2]

Figure 7:
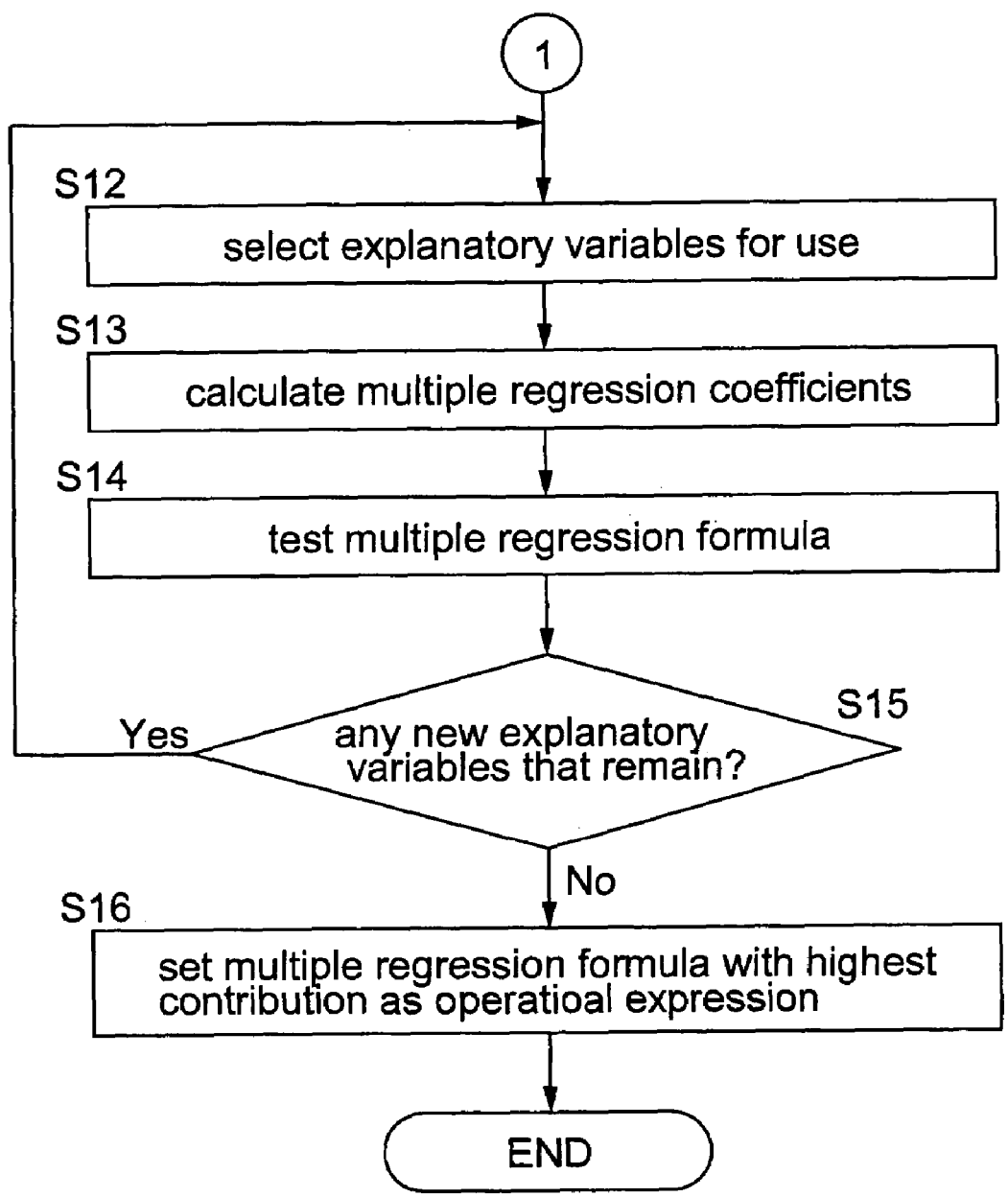
FIG. 7 is a view showing a flow of the second half of the vehicle driver's fatigue evaluating method.

The second half of the vehicle driver's fatigue evaluating method for quantitatively calculating a degree of fatigue A of a driver sitting on a seat 1 will be described with reference to FIG. 7.

As described in preceding section [1], when the data file of loads B2a–B3c and amounts of deflection C2d–C3g and the data file of ratio (K2/K1) have been obtained, a multiple regression analysis is carried out with the loads B2a–B3c and amounts of deflection C2d–C3g serving as explanatory variables and the ratio (K2/K1) as response variable.

First, a desired number of explanatory variables to be used are selected from the data file of loads B2a–B3c and amounts of deflection C2d–C3g (step S12). Next, a regression coefficient of multiple regression analysis is calculated by using the selected explanatory variables and the well-known algorithm of multiple regression analysis (step S13). Then, a contribution of a multiple regression formula obtained in step S13 is calculated, and the multiple regression formula is tested (step S14). While selecting suitable explanatory variables from the plurality of explanatory variables, these steps of multiple regression analysis, i.e. step S12 to step S14, are repeated for each group of selected explanatory variables (step S15).

As noted hereinbefore, various methods are known as methods of selecting optimal explanatory variables from a plurality of explanatory variables. A desired method may be adopted, for example, from among a round robin method for examining regression models of all combinations of the plurality of explanatory variables, a forward selection method for adding one explanatory variable after another, starting with a state of including no explanatory variable, a backward elimination method for subtracting one explanatory variable after another, starting with a state of including all the explanatory variables, and a sequential method for varying the number of explanatory variables.

When the multiple regression analysis based on the selection of conceivable explanatory variables is completed, a multiple regression formula with the highest contribution is specified from the results of the multiple regression analysis. This multiple regression formula is set as operational expression for the vehicle driver's fatigue evaluating method (step S16).

The contribution of the multiple regression formula is the highest where, regarding the data file collected in [1], the amount of rearward deflection C2f in the lower position 2f (lower part) of the backrest portion 2, the load B3a applied downward to the front range 3a (front part) of the seating portion 3 and the load B2a applied rearward to the upper range 2a (upper part) of the backrest portion 2 are set as explanatory variables, and the degree of fatigue A of the driver seated on the seat 1 is set as the ratio (K2/K1) between the viscoelastic property K1 of the muscles of the subject's waist measured in the above step S2 and the viscoelastic property K2 of the muscles of the subject's waist measured in step S8 as response variable.

Consequently, the operational expression for this multiple regression formula is;

$$A(K2/K1) = D1 \cdot C2f + D2 \cdot B3a + D3 \cdot B2a + D4.$$

Coefficient D1, D2, D3 and D4 are, for example, D1=−0.0061, D2=−0.0246, D3=+0.0237, and D4=+1.4076. In the present invention, D1–D4 are not necessarily limited to the above numerical values. In the case of the above operational expression, $R^2=0.46$ has been obtained as coefficient of determination $R^2$ (square of the coefficient of multiple correlation R), i.e. a contribution. That is, although the amount of rearward deflection C2f in the lower position of 2f of the backrest portion 2, the load B3a applied downward to the front range 3a of the seating portion 3 and the load B2a applied rearward to the upper range 2a of the backrest portion 2 greatly influence the degree of fatigue A of the driver seated on the seat 1, the present invention can obtain appropriately the degree of fatigue A of the driver seated on the seat.

[3]

Next, the viscoelastic property K1 of the muscles of the subject's waist measured in the above step S2 described in the foregoing section [1] and the viscoelastic property K2 of the muscles of the subject's waist measured in step S8 will be described.

A piezoelectric element is used as sensor (vibrator). The piezoelectric element is applied to the subject's waist, for example to the part between the third lumbar and fourth lumbar. Next, an operation is carried out to increase pressure on the piezoelectric element gradually, and when the pressure for the piezoelectric element reaches a predetermined value, to decrease pressure on the piezoelectric element gradually. Variations in the vibration frequency of the piezoelectric element occurring during this period are detected.

Figure 5:
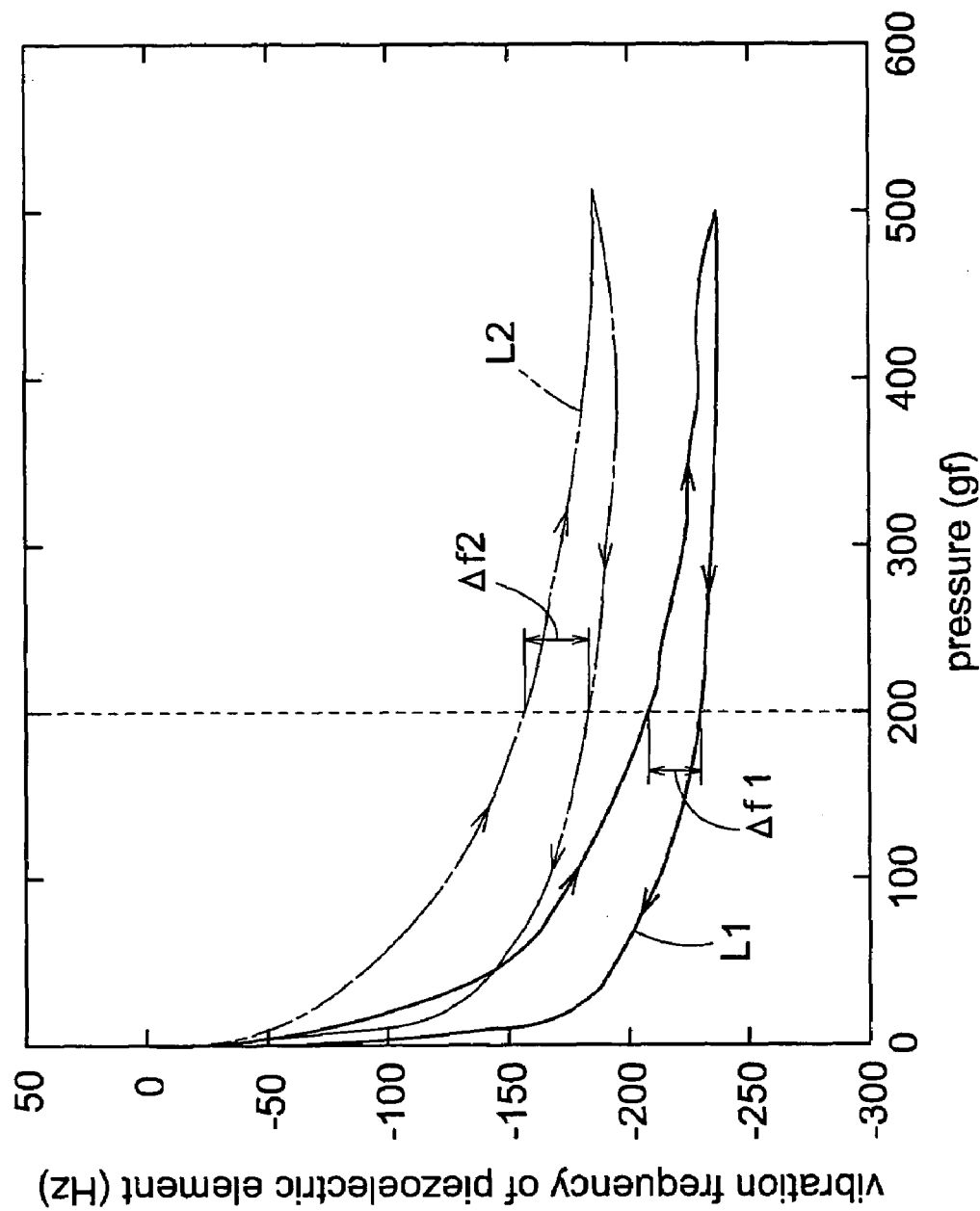
FIG. 5 is a view showing changes in the vibration frequency of a piezoelectric element in time of detecting a viscoelastic property of the muscles in a subject's waist in a vehicle driver fatigue evaluating method.

This state is shown in FIG. 5. The vertical axis in FIG. 5 represents variations in the vibration frequency (hertz Hz) of the piezoelectric elements, while the horizontal axis in FIG. 5 represents pressure (gram force gf) on the piezoelectric element. In step S2, as shown in a solid line L1 in FIG. 5, when the piezoelectric element is applied to the subject's waist and pressure on the piezoelectric element is increased gradually, the vibration frequency of the piezoelectric element lowers gradually from a predetermined vibration frequency. When the pressure on the piezoelectric element becomes about 500 gf, the vibration frequency of the piezoelectric element becomes about −230 Hz. When the pressure on the piezoelectric element is gradually decreased from about 500 gf, the vibration frequency of the piezoelectric element, after stabilizing around −230 Hz for a while, quickly returns to the predetermined vibration frequency.

In this case, a difference $\Delta f1$ is measured between the vibration frequency of the piezoelectric element when the pressure on the piezoelectric element on the increase reaches 200 gf and the vibration frequency of the piezoelectric element when the pressure on the piezoelectric element on the decrease reaches 200 gf, and the difference $\Delta f1$ is regarded as the viscoelastic property K1 of the muscles of the subject's waist. The above solid line L1 shown in FIG. 5 varies with subjects. A different subject results in a different vibration frequency of the piezoelectric element at the time when the pressure on the piezoelectric element reaches about 500 gf.

In step S8, as shown in a long dashed short dashed line L2 in FIG. 5, when the piezoelectric element is applied to the subject's waist and the pressure of the piezoelectric element is increased gradually, the vibration frequency of the piezoelectric element lowers gradually from the predetermined vibration frequency. When the pressure on the piezoelectric element is about 500 gf, the vibration frequency of the piezoelectric element becomes about −180 Hz. When the pressure of the piezoelectric element is gradually decreased from about 500 gf, the vibration frequency of the piezoelectric element, after stabilizing around −180 Hz for a while, quickly returns to the predetermined vibration frequency.

A difference $\Delta f2$ in this case is regarded as the viscoelastic property K2 of the muscles of the subject's waist. The above long dashed short dashed line L2 shown in FIG. 5 varies with subjects. A different subject results in a different vibration frequency of the piezoelectric element at the time when the pressure on the piezoelectric element reaches about 500 gf.

As described above, the difference $\Delta f1$ is regarded as the viscoelastic property K1 of the muscles of the subject's waist, and the difference $\Delta f2$ as the viscoelastic property K2 of the muscles of the subject's waist. A ratio ($\Delta f2/\Delta f1$) between the difference $\Delta f1$ and difference $\Delta f2$ is regarded as an actual degree of fatigue measured of the driver seated on the seat 1. This actual degree of fatigue is used as the response variable in the foregoing section [2], to calculate the degree of fatigue A of the driver seated on the seat 1.

[4]

Next, a vehicle seat evaluating apparatus will be described, which apparatus uses the vehicle driver's fatigue evaluating method described in foregoing sections [1]–[3].

Figure 1:
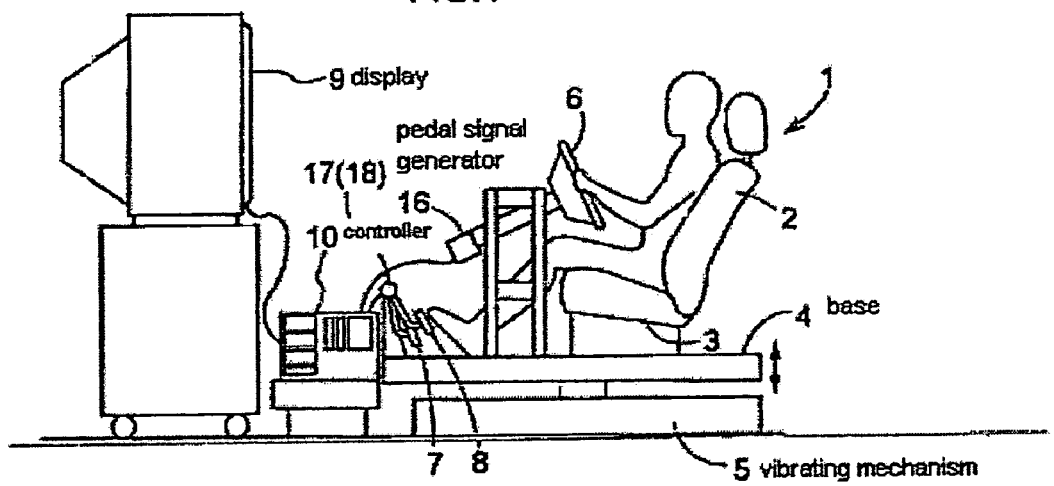
FIG. 1 is a side elevation of a vehicle seat evaluating apparatus.

FIG. 1 shows the vehicle seat evaluating apparatus which includes a base 4 supporting a seat 1 to be evaluated, and a vibrating mechanism 5 for applying vibrations in various running states of a vehicle to the base 4 (which is capable of applying vibrations in vertical directions, fore and aft directions and transverse directions to the base 4). The base 4 has a steering wheel 6, an accelerator pedal 7 and a brake pedal 8. A display 9 and a controller 10 are arranged forwardly of the base 4.

Figure 2:
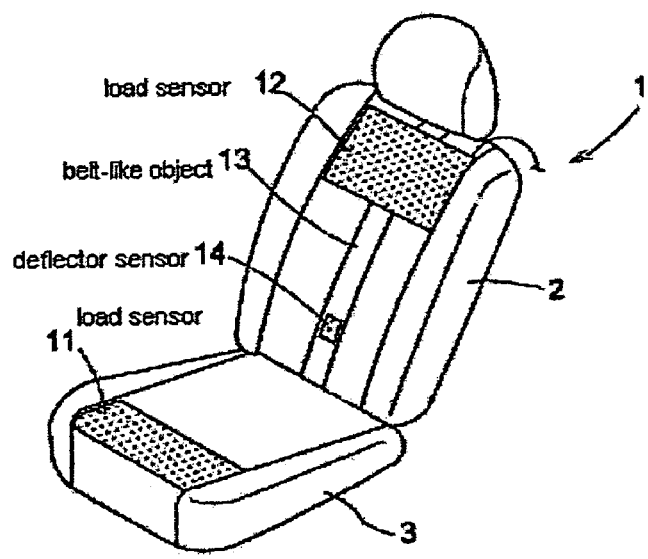
FIG. 2 is a perspective view showing a state where load sensors and a deflection sensor of the vehicle seat evaluating apparatus are attached to a seat.

As shown in FIG. 2, soft load sensors 11 and 12 in sheet form are provided with numerous pressure sensors (not shown) arranged at predetermined intervals. A thin belt-like object 13 made of cloth is connected to the load sensor 12. The belt-like object 13 has a deflection sensor 14.

Figure 3:
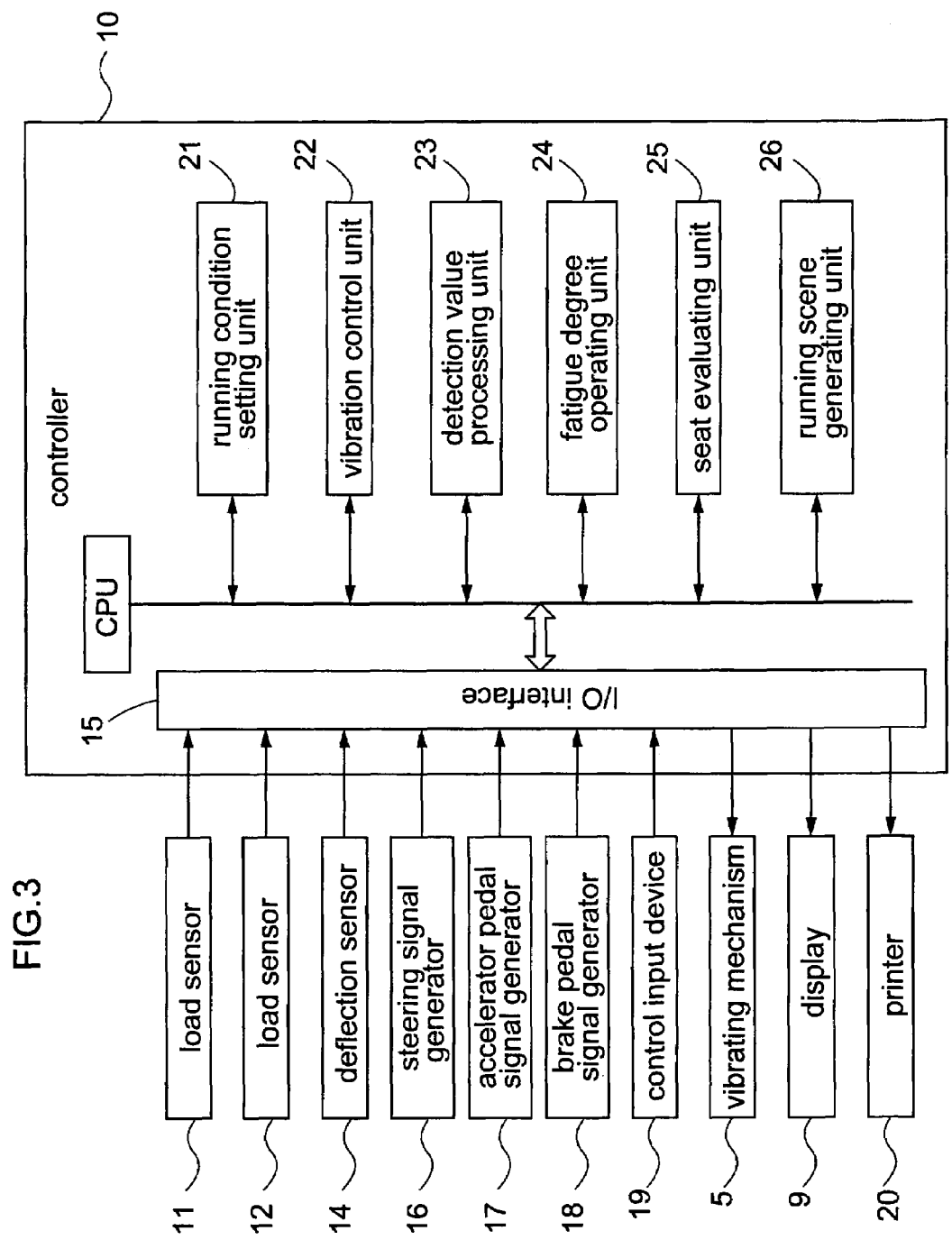
FIG. 3 is a block diagram showing a controller the vehicle seat evaluating apparatus.

As shown in FIGS. 1 and 3, the controller 10 has a microcomputer acting as a core element thereof. Connected to the controller 10 through an I/O interface 15 are the load sensors 11 and 12, the deflection sensor 14, a steering signal generator 16 for generating signals based on operation of the steering wheel 6, an accelerator pedal signal generator 17 for generating signals based on depression of the accelerator pedal 7, a brake pedal signal generator 18 for generating signals based on depression of the brake pedal 8, a control input device 19 such as a keyboard, the vibrating mechanism 5, the display 9 and a printer 20.

As shown in FIG. 3, the controller 10 includes a running condition setting unit 21 for setting running conditions based on the signals of the control input device 19, steering signal generator 16, accelerator pedal signal generator 17 and brake pedal signal generator 18, a vibration control unit 22 for causing the vibrating mechanism 5 to generate vibrations according to the running conditions set by the running condition setting unit 21 and the signals of the steering signal generator 16, accelerator pedal signal generator 17 and brake pedal signal generator 18, a detection value processing unit 23 for processing detection values of the load sensors 11 and 12 and deflection sensor 14, a fatigue degree operating unit 24 for calculating a degree of fatigue A of the driver seated on the seat 1 based on results of processing by the detection value processing unit 23, a seat evaluating unit 25 for evaluating the seat 1 based on the degree of fatigue A calculated by the fatigue degree operating unit 24, and a running scene generating unit 26 for causing the display 9 to display running scenes according to the signals of the running conditions set by the running condition setting unit 21, steering signal generator 16, accelerator pedal signal generator 17 and brake pedal signal generator 18.

[5]

Next, a method of evaluating the seat 1 (vehicle seat valuating method) will be described with reference to FIG. 8, which method uses the vehicle seat evaluating apparatus described in the preceding section [4].

As shown in FIGS. 1 and 2, the seat 1 to be evaluated is provided, and the seat 1 is attached to the base 4 (step S21). The load sensor 11 is attached to a front part of a seating portion 3, and the load sensor 12 is attached to an upper part of a backrest portion 2. As described in the preceding section [4], the thin belt-like object 13 made of cloth is connected to the load sensor 12. The belt-like object 13 has the deflection sensor 14. When the load sensor 12 is attached to the upper part of the backrest portion 2 as noted above, the deflection sensor 14 is located on the lower part of the backrest portion 2 (step S22).

Running conditions (high-speed running state, urban area running state, off-road running state, etc.) are set and inputted from the control input device 19 (step S23). When a subject sits down on the seat 1 (step S24), an evaluation of the seat 1 is started. When the evaluation of the seat 1 is started, the vibrating mechanism 5 generates vibrations according to the running conditions set in step S23 and the signals of the steering signal generator 16, accelerating signal generator 17 and brake pedal signal generator 18, and running scenes are displayed on the display 9 (step S25).

During this period, upon lapse of each predetermined time, the deflection sensor 14 detects an amount of rearward deflection C2f in the lower part of the backrest portion 2, the load sensor 11 detects a load B3a (an average of detection values of the numerous pressure sensors included in the load sensor 11) applied downward to the front part of the seating portion 3, and the load sensor 12 detects a load B2a (an average of detection values of the numerous pressure sensors included in the load sensor 12) applied rearward to the upper part of the backrest portion 2 (step S26).

In this case, in step S26, averages of detection values obtained upon lapse of each predetermined time are regarded as the amount of rearward deflection C2f in the lower part of the backrest portion 2, the load B3a applied downward to the front part of the seating portion 3, and the load B2a applied rearward to the upper part of the backrest portion 2, or detection values detected immediately after an end are regarded as the amount of rearward deflection C2f in the lower part of the backrest portion 2, the load B3a applied downward to the front part of the seating portion 3 and the load B2a applied rearward to the upper part of the backrest portion 2.

Based on the above amount of rearward deflection C2f in the lower part of the backrest portion 2, the load B3a applied downward to the front part of the seating portion 3 and the load B2a applied rearward to the upper part of the backrest portion 2, the degree of fatigue A of the driver seated on the seat 1 is calculated by the vehicle driver's fatigue evaluating method (operational expression) described in the foregoing sections [1]–[3] (steps S27 and S28). When changing running conditions (high-speed running state, urban area running state, off-road running state, etc.) for the same seat 1 (step S29), running conditions are inputted from the control input device 19 (step S23), and the above steps S25–S28 are repeated. Then, evaluation results of the seat 1 (such as the degree of fatigue A of the driver seated on the seat 1) are outputted to the printer 20 (step S30).

Based on the vehicle seat evaluating method, the shape and material of a seat may be changed, thereby to obtain a seat producing a reduced degree of fatigue of the driver seated on the seat.

The invention claimed is:

1. A vehicle driver's fatigue evaluating method for quantitatively calculating a degree of fatigue of a driver seated on a seat by using an operational expression determined by a statistical technique based on load measurements comprising an amount of rearward deflection of a lower part of a backrest portion of the seat, a load applied downward to a front part of a seating portion of the seat, and a load applied rearward to an upper part of the backrest portion, in a state of the driver being seated on the seat, wherein said operational expression is obtained by a multiple regression analysis with the amount of rearward deflection of the lower part of the backrest portion, the load applied downward to the front part of the seating portion and the load applied rearward to the upper part of the backrest portion regarded as explanatory variables, and an actual degree of fatigue measured of the driver seated on the seat as a response variable, and storing load measurements and a degree of fatigue of a driver in a data file.

2. The vehicle driver's fatigue evaluating method as defined in claim 1, wherein said actual degree of fatigue is derived from a viscoelastic property of waist muscles of the driver seated on the seat.

3. A vehicle seat evaluating apparatus comprising:
a first detecting device for detecting an amount of rearward deflection of a lower part of a backrest portion of a seat, a second detecting device for detecting a load applied downward to a front part of a seating portion of the seat, and a third detecting device for detecting a load applied rearward to an upper part of the backrest portion, in a state of the driver being seated on the seat;
a calculating device for quantitatively calculating a degree of fatigue of the driver seated on the seat by using an operational expression determined by a statistical technique based on detection values of said first, second and third detecting devices, wherein said operational expression is obtained by a multiple regression analysis with the amount of rearward deflection of the lower part of the backrest portion, the load applied downward to the front part of the seating portion and the load applied rearward to the upper part of the backrest portion regarded as explanatory variables, and an actual degree of fatigue measured of the driver seated on the seat as a response variable; and
an evaluating device for evaluating the seat by the degree of fatigue calculated by said calculating device.

4. A vehicle seat evaluating method for evaluating a seat with a degree of fatigue calculated by a vehicle driver's fatigue evaluating method for quantitatively calculating a degree of fatigue of a driver seated on the seat and storing load measurements and a degree of fatigue of a driver in a data file, the degree of fatigue of the driver seated on the seat is calculated by using an operational expression determined by a statistical technique based on an amount of rearward deflection of a lower part of a backrest portion of the seat, a load applied downward to a front part of a seating portion of the seat, and a load applied rearward to an upper part of the backrest portion, in a state of the driver being seated, wherein said operational expression is obtained by a multiple regression analysis with the amount of rearward deflection of the lower part of the backrest portion, the load applied downward to the front part of the seating portion and the load applied rearward to the upper part of the backrest portion regarded as explanatory variables, and an actual degree of fatigue measured of the driver seated on the seat as a response variable.

5. A vehicle seat evaluating method as defined in claim 4 wherein said actual degree of fatigue is derived from a viscoelastic property of waist muscles of the driver seated on the seat.

* * * * *

UNITED STATES PATENT AND TRADEMARK OFFICE
CERTIFICATE OF CORRECTION

PATENT NO. : 7,248,996 B2  Page 1 of 1
APPLICATION NO. : 10/525931
DATED : July 24, 2007
INVENTOR(S) : Uenishi et al.

It is certified that error appears in the above-identified patent and that said Letters Patent is hereby corrected as shown below:

<u>Title Page</u>, see Item (56) References Cited, FOREIGN PATENT DOCUMENTS, insert the following:

-- JP        07336943      12/1995
   WO       00/44580      8/2000 --

<u>Column 3</u>, Line 66, "controller the" should read -- controller of the --

Signed and Sealed this

Twenty-seventh Day of November, 2007

JON W. DUDAS
*Director of the United States Patent and Trademark Office*